United States Patent
Samburski et al.

(10) Patent No.: US 11,760,716 B2
(45) Date of Patent: Sep. 19, 2023

(54) DRUG CRYSTALLIZATION UNDER MICROGRAVITY CONDITIONS

(71) Applicant: SPACEPHARMA R&D ISRAEL LTD., Herzliya (IL)

(72) Inventors: Guy Samburski, Beit Yitzhak (IL); Shimon Amselem, Rehovot (IL)

(73) Assignee: SPACEPHARMA R&D ISRAEL LTD., Herzliya (IL)

( * ) Notice: Subject to any disclaimer, the term of this patent is extended or adjusted under 35 U.S.C. 154(b) by 0 days.

(21) Appl. No.: 17/262,710

(22) PCT Filed: Jul. 23, 2019

(86) PCT No.: PCT/IL2019/050835
§ 371 (c)(1),
(2) Date: Jan. 23, 2021

(87) PCT Pub. No.: WO2020/021547
PCT Pub. Date: Jan. 30, 2020

(65) Prior Publication Data
US 2021/0300861 A1    Sep. 30, 2021

Related U.S. Application Data

(60) Provisional application No. 62/702,365, filed on Jul. 24, 2018.

(51) Int. Cl.
*C07C 213/10*    (2006.01)
*C07B 63/00*    (2006.01)

(52) U.S. Cl.
CPC ............ *C07C 213/10* (2013.01); *C07B 63/00* (2013.01); *C07B 2200/13* (2013.01)

(58) Field of Classification Search
CPC .... C07C 213/10; C07B 63/00; C07B 2200/13
See application file for complete search history.

(56) References Cited

U.S. PATENT DOCUMENTS

| 5,173,087 A | 12/1992 | Kroes et al. |
| 6,027,565 A | 2/2000 | Bugg et al. |
| 2015/0239862 A1 | 8/2015 | Dammalapati et al. |

OTHER PUBLICATIONS

El-Zein, H. et al. Asian Journal of Pharmaceutical Sciences 10 (2015) 283-291.*
Scaife, Charles WJ, et al., "Crystallization in Space: Implications for Molecular Sieve Synthesis", Novel Materials in Heterogeneous Catalysis, Chapter 1, pp. 2-13, 1990.
Vergara, A., Lorber, B., Zagari, A., & Giegé, R. (2003). Physical aspects of protein crystal growth investigated with the Advanced Protein Crystallization Facility in reduced-gravity environments. *Acta Crystallographica Section D: Biological Crystallography*, 59(1), pp. 2-15.
Search Report of International Patent Application No. PCT/IL2019/050835, dated Sep. 24, 2019.
Extended European Search Report for EP appication No. EP19839983.4 dated Mar. 16, 2022.

* cited by examiner

*Primary Examiner* — Sikarl A Witherspoon
(74) *Attorney, Agent, or Firm* — PEARL COHEN ZEDEK LATZER BARATZ LLP

(57) ABSTRACT

Disclosed is a method for crystallizing molecules having a molecular weight equal to or lower than about 500 Dalton in a gravity below about 0.01 g to about 0.000001 g as well as to crystalline molecules having a molecular weight equal to, or lower than, about 500 Dalton, prepared under microgravity conditions.

14 Claims, 3 Drawing Sheets

DRUG CRYSTALLIZATION UNDER MICROGRAVITY CONDITIONS

CROSS-REFERENCE TO RELATED APPLICATIONS

This application is a US National Phase Application of PCT International Patent Application No. PCT/IL2019/050835, International Filing Date Jul. 23, 2019, claiming the benefit of U.S. Provisional Patent Application No. 62/702,365, filed Jul. 24, 2018, which is hereby incorporated by reference.

FIELD OF THE INVENTION

This invention is directed to a method for crystallizing molecules, e.g., active pharmaceutical ingredients (APIs), having a molecular weight equal to, or lower than, about 500 Dalton, wherein the crystallization is performed at a gravity below about 0.01 g to about 0.000001 g, e.g., in outer-space. Additionally, the invention is directed to crystalline molecules, such as APIs, having a molecular weight equal to or lower than about 500 Dalton, which were crystalized at a gravity below about 0.01 g to about 0.000001 g, e.g., in outer-space. The invention is further directed to crystalline molecules, such as APIs, having a molecular weight equal to or lower than about 500 Dalton.

BACKGROUND OF THE INVENTION

Many small molecules, including APIs, are known in the art. Many uses of such molecules require the crystallization thereof; however, known crystallization methods do not always provide the required crystals, having properties, e.g., for the preparation of drug formulations.

Vilanterol, 4-{(1R)-2-[(6-{2-[(2,6-dichlorobenzyl) oxy] ethoxy} hexyl)amino]-1-hydroxyethyl}-2-(hydroxymethyl) phenol, is an example of a small molecule API in which the formed crystals are not optimal. Particularly, vilanterol is a selective long-acting beta2-adrenergic agonist (LABA) with inherent 24-hour activity for once daily treatment of chronic obstructive pulmonary disease (COPD) and asthma. The pharmacological effect of vilanterol is attributable to the stimulation of intracellular adenylyl cyclase, which catalyzes the conversion of adenosine triphosphate (ATP) to cyclic-3',5'-adenosine monophosphate (cAMP). Increases in cyclic AMP are associated with the relaxation of bronchial smooth muscle as well as with the inhibition of the release of hypersensitivity mediators from mast cells in the lungs.

The chemical structure of vilanterol is:

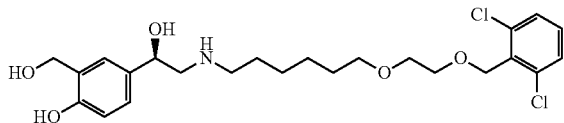 [SMILES: OCc1cc([C@@H](O)CNCCCCCCOCCOCc2c(Cl)cccc2Cl)ccc1O]

Many efforts have been devoted in recent years to the crystallization of vilanterol; however, to date, it has been proven difficult to prepare high quality single crystals for the purpose of optimal formulation or crystallography.

Methods for crystallizing macromolecules, such as proteins in microgravity are known; however, no such methods exist for crystallizing small molecules, e.g., APIs. Further, there is no known evidence of improved crystal morphology or new polymorphs formed by the preparation of small molecule crystals in microgravity. In addition, it is known that crystallization methods are dependent on the size of the molecule and therefore, the known methods for macromolecules are irrelevant to any type of small molecule.

SUMMARY OF THE INVENTION

Embodiments of the invention are directed to a method for crystallizing molecules, wherein the method comprises:
 placing a molecular substance having a molecular weight equal to or lower than about 500 Dalton in a microgravity environment, wherein the microgravity environment has a gravitational acceleration in a range of below about 0.01 g to about 0.000001 g;
 crystalizing molecules of the molecular substance in the microgravity environment, thereby obtaining at least one crystalline polymorph in the microgravity environment; and
 removing the at least one crystalline polymorph from the microgravity environment by transferring it into an environment having a gravitational acceleration of 1 g.

According to some embodiments, the method is performed in outer space.

According to some embodiments, the molecules are crystallized by adding an anti-solvent to a solution of the molecules, by cooling a saturated solution of the molecule, by reacting the solution of the molecules with a solution containing ions, thereby forming an insoluble salt of the molecule, or by changing the pH of a solution comprising the molecules, thereby causing the molecules to precipitate in crystalline form.

According to some embodiments, the molecule is an active pharmaceutical ingredient (API). According to some embodiments, the molecule is vilanterol, a corticosteroid, a bronchodilator, a prostaglandin analogue or an anti-schizophrenic agent.

Further embodiments of the invention are directed to a method for the preparation of vilanterol crystals, wherein the method comprises:
 placing vilanterol in a microgravity environment having a gravitational acceleration in a range of 0.01 g to about 0.000001 g;
 crystalizing the vilanterol, thereby obtaining at least one crystalline polymorph of vilanterol in the microgravity environment; and
 removing the at least one crystalline polymorph of vilanterol from the microgravity environment by transferring at least one crystalline polymorph of vilanterol into an environment having a gravitational acceleration of 1 g.

According to some embodiments, the vilanterol is crystallized by the gradual cooling of a saturated solution of vilanterol in a solvent. According to some embodiments, the solvent is a polar organic solvent or a combination of polar organic solvents. According to some embodiments, the polar organic solvent is an organic alcohol or a combination of organic alcohols. According to some embodiments, the organic alcohol is ethanol, methanol, iso-propyl alcohol, or any combination thereof.

According to some embodiments, the method comprises (i) placing a saturated solution of vilanterol in the microgravity environment or preparing a saturated solution of vilanterol in a microgravity environment and (ii) subsequently to step (i), cooling the saturated solution in order to provide crystalline vilanterol.

According to some embodiments, the vilanterol is crystallized by the addition of an anti-solvent to a vilanterol solution comprising vilanterol and a solvent. According to some embodiments, the solvent is a polar organic solvent or a combination of polar organic solvents. According to some embodiments, the polar organic solvent is an organic alcohol or a combination of organic alcohols. According to some embodiments, the organic alcohol is ethanol, methanol, iso-propyl alcohol, or any combination thereof. According to some embodiments, the anti-solvent is a non-polar organic solvent or any combination of non-polar organic solvents. According to some embodiments, the anti-solvent is hexane, cyclohexane, heptane, pentane or any combination thereof.

According to some embodiments, the method comprises placing a solution of vilanterol in a microgravity environment or preparing a solution of vilanterol in a microgravity environment and subsequently, adding an anti-solvent to the vilanterol solution, thereby providing crystalline vilanterol.

Further embodiments of the invention are directed to a crystalline API having a molecular weight equal to, or lower than, about 500 Dalton, prepared under microgravity conditions. According to some embodiments, the API is vilanterol.

According to some embodiments, the method of the invention further comprises preparing crystals in an environment having a gravitational acceleration of 1 g by seeding with the at least one crystalline polymorph prepared under microgravity.

According to some embodiments, the crystals prepared in an environment having a gravitational acceleration of 1 g have at least one crystalline property in common with the seeding crystals, prepared under microgravity, the crystalline property being selected from the group consisting of polymorph form, crystal habit, aspect ratio and particle size distribution.

BRIEF DESCRIPTION OF THE DRAWINGS

Embodiments of the invention will be understood and appreciated more fully from the following detailed description in conjunction with the figures, which are not to scale, in which like reference numerals indicate corresponding, analogous or similar elements, and in which:

FIG. 1A shows a front view of a cassette, comprising main compartments, storage/waste compartments and a rubber container; FIG. 2B shows a back view of the cassette, presenting the storage/waste compartments and the rubber container; FIG. 2C illustrates a rubber (Viton®) container and several elements thereof; and FIG. 2D presents a schematic description of an embodiment of the invention;

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Throughout this description, the term "about" is intended to cover ±10% of the specifically disclosed value.

It is noted that herein, microgravity is defined as a gravitational acceleration below about 0.01 g to about 0.000001 g, as may be obtained in space, for example. Further, the terms "gravity", "gravitational acceleration" and the like are interchangeable unless specifically mentioned otherwise, or unless a person skilled in the art would have understood otherwise. It is further noted that terms, such as "space grown crystals", "crystals grown in microgravity" or "crystals grown at a gravity below about 0.01 g to about 0.000001 g" are interchangeable, unless specifically mentioned otherwise, or unless a person skilled in the art would have understood otherwise. A gravitational acceleration of 1 g refers to the gravitational environment on earth.

It is further noted that throughout this description, the terms "space", "outer space" "in orbit" and the like are interchangeable unless specifically mentioned otherwise, or unless a person skilled in the art would have understood otherwise.

It is further noted that the storage compartments according to the invention may be used also as waste compartments and therefore, unless specifically mentioned otherwise, or unless a person skilled in the art would have understood otherwise, the term "storage compartment", "waste compartment" and "storage/waste compartment" are interchangeable.

Embodiments of the invention are directed to a method for crystallizing molecules, e.g., APIs, having a molecular weight equal to or lower than about 500 Dalton in a gravity of below about 0.01 g to about 0.000001. According to some embodiments, the method is performed in space.

Figure 1:
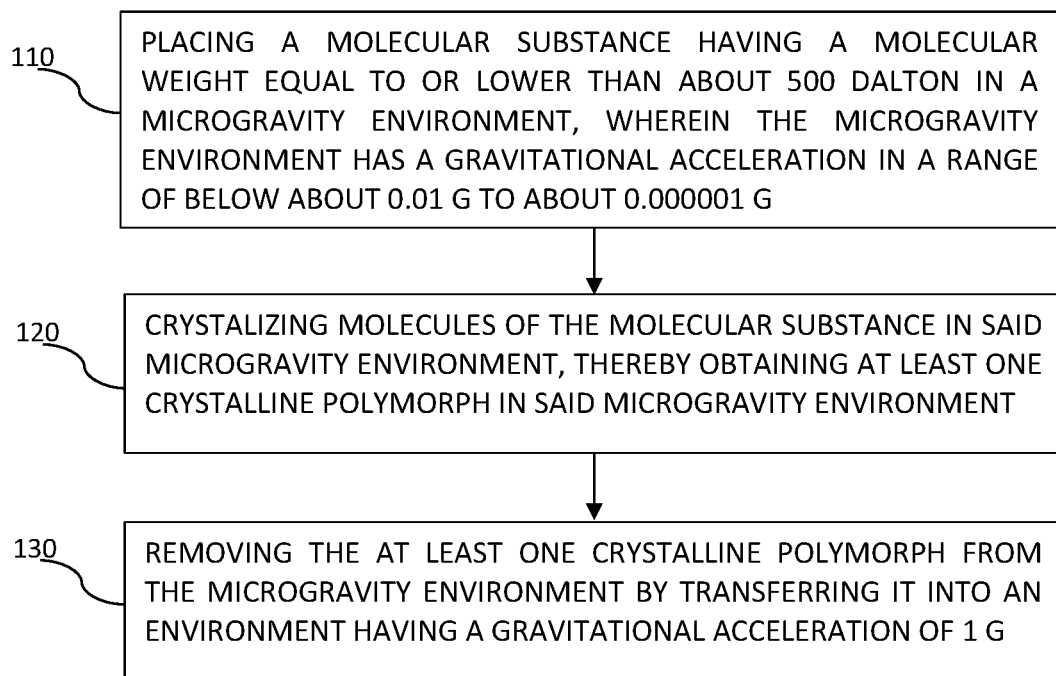
FIG. 1 is a flowchart of a method for crystallizing molecules according to some embodiments of the invention.

Reference is made to FIG. 1 which is a flowchart of a method for crystallizing molecules according to some embodiments of the invention. The method of FIG. 1 may be preformed in systems or devices disclosed herein below with respect to FIGS. 2A-2D or using any other suitable device.

According to some embodiments, the method may include:

in step 110, placing a molecule having a molecular weight equal to or lower than about 500 Dalton in a microgravity environment;

in step 120, crystalizing the molecule, thereby obtaining at least one crystalline polymorph in the microgravity environment; and in step 130, removing the at least one crystalline polymorph from the microgravity environment by transferring it into an environment having a gravity of 1 g.

In some embodiments, the molecule having the molecular weight equal to or lower than about 500 Dalton may be one of: vilanterol, a corticosteroid, a bronchodilator, a prostaglandin analogue or an anti-schizophrenic agent and the like.

In some embodiments, the molecule may be crystalized in microgravity, in step 120, using any known crystallization method, such as controlled cooling of a solution of the molecule, or adding an anti-solvent to it. In both methods, seeding can be used to control the onset of crystallization. The crystallization methods may be performed in a continuous form, e.g., in a plug-flow reactor, wherein the anti-solvent may be added in single, double or multiple addition points. According to some embodiments, a solution comprising the molecule to be crystalized may be dispersed as droplets in a continuous oily phase, which may lower the effect of shear-forces on the growing crystals. This may also enable the performance of multiple experiments in one reactor, wherein the experiments may be performed sequentially. According to some embodiments, a saturated solution comprising the molecule to be crystalized may be cooled in order to allow crystals to form. Crystalline seeds of the pure molecule may also be added, thereby controlling the level of supersaturation and the kinetics of the crystalline growth. According to some embodiments, a dissolved base may be reacted with an acid in order to produce a non-soluble salt of the molecule to be crystalized, e.g., an active pharmaceutical ingredient.

It is noted that any of the above crystallization methods may be performed in either batch mode or in a continuous mode by means of plug-flow reactor or an agitated continuous reactor. Further, all of the above crystallization methods, as well as any other contemplated crystallization method, may be performed in either Earth-like gravity, microgravity, or reduced gravity, e.g., gravity that simulates the conditions on the moon (about 0.165 of Earth gravity) or on any other planet, as desired, e.g., Mars gravity, which is about 0.34 of Earth gravity.

According to some embodiments, the microgravity conditions are provided by performing the step of crystallization in space. According to some embodiments, the removal of the prepared crystals from the microgravity environment is performed by returning the crystalline polymorph(s) from space to earth.

According to some embodiments, the molecule is vilanterol.

Embodiments of the invention are directed to a method for the preparation of vilanterol crystals, wherein the method comprises:

placing vilanterol in a microgravity environment;
crystalizing the vilanterol, thereby obtaining at least one crystalline polymorph of vilanterol in the microgravity environment; and
removing the at least one crystalline polymorph of vilanterol from the microgravity environment by transferring the at least one crystalline polymorph of vilanterol into an environment having a gravity of 1 g.

According to some embodiments, the vilanterol is crystallized by the gradual cooling of a saturated solution of vilanterol in a solvent. According to some embodiments, the solvent is ethanol, methanol, iso-propyl alcohol, or any combination thereof. Thus, the method comprises placing a saturated solution of vilanterol in a microgravity environment, or preparing a saturated solution of vilanterol in a microgravity environment, and subsequently, cooling the saturated solution in order to provide crystalline vilanterol. In some embodiments of the invention, the gradual cooling of the vilanterol ethanolic solution container is carried out by reducing the temperature from about 37° C. to about 4° C. by storing the container in a refrigerator until the return to Earth.

According to some embodiments, the vilanterol is crystallized by the addition of an anti-solvent to a vilanterol solution. According to some embodiments, the solvent is ethanol, methanol, iso-propyl alcohol, any other appropriate type of organic alcohol or polar organic solvent, or any combination thereof. According to some embodiments, the anti-solvent is hexane, cyclo-hexane, heptane, pentane, any other appropriate non-polar organic solvent, or any combination thereof. The addition of the anti-solvent may be performed at an ambient temperature. According to some embodiments, cooling to about 4° C. may increase the yield of the crystallization. Thus, the method comprises placing a solution of vilanterol in a microgravity environment, or preparing a solution of vilanterol in a microgravity environment, and subsequently, adding an anti-solvent to the vilanterol solution, thereby providing crystalline vilanterol.

According to some embodiments, the crystalline vilanterol comprises one polymorph.

Some embodiments of the invention are further directed to crystalline molecules, e.g., APIs, having a molecular weight equal to, or lower than, about 500 Dalton, prepared under microgravity conditions. The molecules may be, for example, a drug used for respiratory dosage forms, ophthalmic or topical applications, as well as controlled release form drugs, which require high-quality crystals. Specific non-limiting examples for drugs that may be crystallized according to this invention include corticosteroids, such as fluticasone, betamethasone and the like, bronchodilators, such as salbutamol, prostaglandin analogues, such as latanoprost, anti-schizophrenic agents, such as risperidone or paliperidone.

According to some embodiments, the molecule, e.g., the API, may exhibit a different polymorph when crystallized under micro-gravity, in comparison to being crystalized under earth gravity, thereby providing unique pharmacokinetic properties. Accordingly, the invention is further directed to crystalline molecules, such as APIs, having a molecular weight equal to or lower than about 500 Dalton.

The invention is further directed to the preparation of crystals under about 1 g gravity by seeding with crystals prepared under microgravity, e.g., in space. For example, vilanterol crystals may be prepared on earth, under 1 g gravity, by seeding with vilanterol crystals prepared under microgravity conditions, e.g., in space. According to some embodiments, due to the seeding with crystals prepared under microgravity, even though the crystals are prepared under about 1 g gravity, their properties will be identical to those of the seeding crystals, i.e., the crystals grown under microgravity.

Figure 2A:
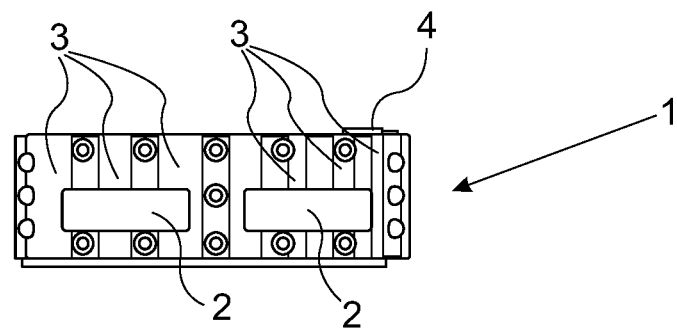
FIGS. 2A, 2B, 2C and 2D present a miniaturized lab that may be used on microgravity platforms, according to some embodiments, e.g., in space missions.
Figure 2B:
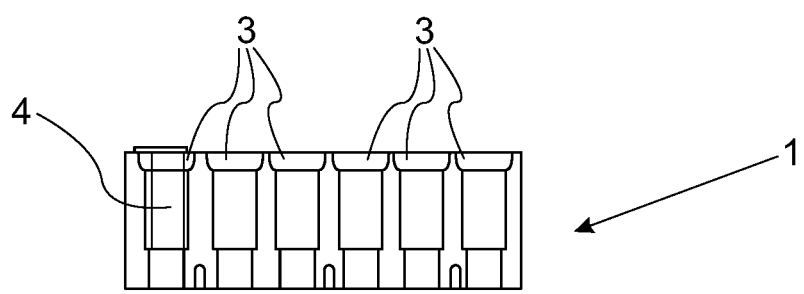
Figure 2C:
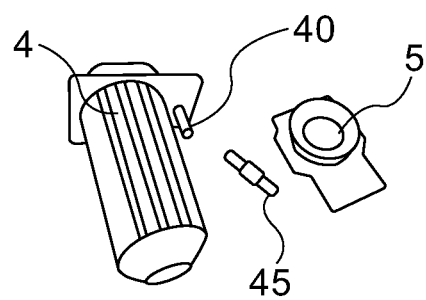

Reference is now made to FIGS. 2A, 2B, 2C and 2D, presenting embodiments of the system used for the invention. FIGS. 2A and 2B present cassette (1) having two main compartments (2), each of which is connected to three separate storage/waste compartments, wherein each storage/waste compartment (3) may comprise rubber container (4) (for sake of simplicity only one rubber container (4) is shown). As shown in FIG. 2C, each rubber container (4) may be equipped with cover (5), tube (40) and tube reinforcement (45), wherein tube reinforcement (45) may be positioned within tube (40) in order to reinforce tube (40) and to connect tube (40) to internal system (7), as shown in FIG. 1D.

It is noted that not necessarily all compartments are used, for example, only one or two of the three storage/waste compartments may be utilized, and further, the number of compartments may vary according to embodiments of the invention.

The main compartment (2) (FIGS. 2A and 2D) may be prepared from Polysulfone or similar polymer, and may have any appropriate volume, e.g., between about 0.5-5 ml, or specifically, the main compartment (2) may have a volume of about 0.5, 1, 2, 3, 4 or 5 ml. Each storage/waste compartment (3) (see FIGS. 2A, 2B and 2D) may contain rubber (possibly fluoroelastomers, such as Viton®) container (4) (shown separately in FIG. 2C), in which fluid may be stored. The volume of each storage/waste compartment (3) may be between about 0.5-5 ml, or specifically, each storage/waste compartment (3) may have a volume of about 0.5, 1, 2, 3, 4 or 5 ml. The fluids in main compartment (2) may be mixed with the fluids from the rubber containers (4) attached thereto by activation of a designated plunger, which is used for the activation and in order to release the anti-solvent from the reservoir, as detailed herein.

Figure 2D:
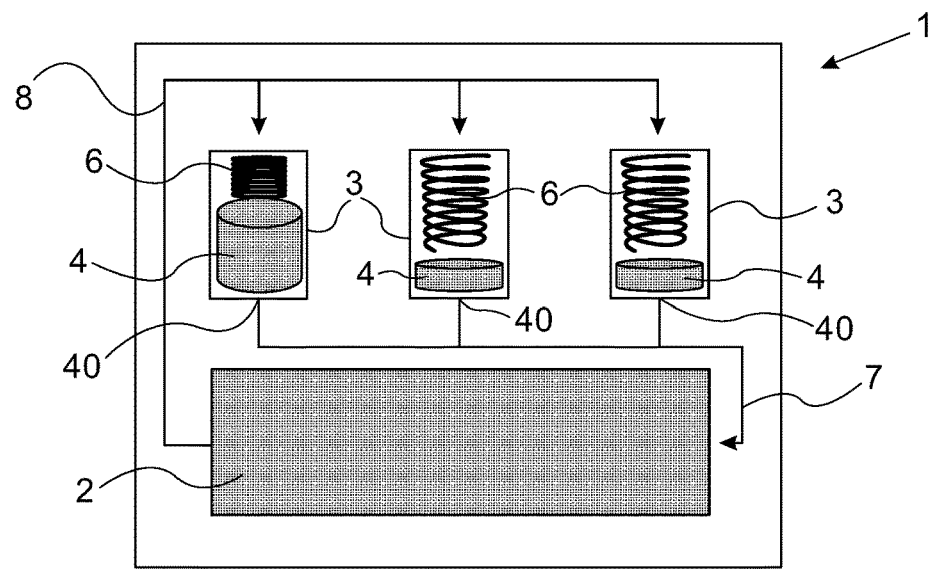

Reference is now made to FIG. 2D, presenting a schematic description of an embodiment of the invention, showing cassette (1) comprising main compartment (2), which is attached by internal systems (7) and (8) to three separate storage/waste compartments (3). As shown in FIG. 1D, each storage/waste container may contain a rubber container (4), wherein each rubber container (4) is operated by designated plunger (6). Particularly, as shown in FIG. 1D, plunger (6) is a spring-like element, which may be operated electronically. Plunger (6) is positioned in storage/water compartments (3) adjacent to rubber container (4). Before being operated, plunger (6) is in its compressed form under rubber container (4) (see, e.g., the left-hand storage/waste compartments (3) in FIG. 2D). When plunger (6) is operated, i.e., the spring element is released, possibly electronically, plunger (6) is transferred to its extended form and presses against rubber container (4), which is thereby compressed, as shown in the middle and right hand storage/waste compartments (3) in FIG. 2D. The compression of rubber container (4) causes liquid found within rubber container (4) to flow out through tube (40) (see also FIG. 2C) and then, via internal system (7), into main compartment (2). Any waste or overflow from main compartment (2) may be transferred back into storage/waste compartment (3) via internal system (8), wherein the waste or overflow may fill or partially fill the area in which plunger (6) is positioned in storage/waste compartment (3), i.e., under compressed rubber container (4) (or above compressed rubber container (4)—depending on the design of cassette (1)). It is noted that while FIGS. 2A, 2B, 2C and 2D present a specific embodiment of cassette (1), any other alternative embodiments may be contemplated, e.g., having separate compartments for the waste and for the storage, having any number of main chambers, compartments attached thereto and rubber containers positioned therein, filling any number of compartments/rubber containers, leaving any number of compartments/rubber containers empty and the like.

Unless explicitly stated, the method embodiments described herein are not constrained to a particular order or sequence. Additionally, some of the described method embodiments or elements thereof can occur or be performed simultaneously, at the same point in time, or concurrently.

Various embodiments have been presented. Each of these embodiments may of course include features from other embodiments presented, and embodiments not specifically described may include various features described herein.

EXAMPLES

The experiments detailed below were included in SpacePharma's NEXUS mission to the International Space Station (ISS), which launched on Nov. 11, 2017 from Wallop Island (Virginia, US) on board of Orbital A8 rocket, connected to the ISS through Cygnus docking on Nov. 13, 2017 and returned to Earth on Jan. 13, 2018 in a Space-X Dragon CRS-13 mission. SpacePharma's NEXUS lab was a miniaturized, automated, remote-controlled lab operated by researchers on Earth, without the need for astronauts' involvement. The technology provided fast, cost-effective access to microgravity. Nexus was the first-ever life-science research device onboard the ISS to be operated and controlled directly by researchers on Earth.

Example 1—Setup of Nexus Lab for Vilanterol for Crystallization Experiments

The microgravity system of the invention was a miniaturized lab developed for microgravity platforms including space missions. The lab was fully automated and was remotely controlled from earth. Each experiment contained cassette (1) having main compartment (2) and three storage/waste compartments (3) connected directly to the main compartment, wherein each storage/waste compartment (3) comprises rubber container (4), which is equipped with cover (5), tube (40) and tube reinforcement (45), as shown in FIGS. 2A, 2B and 2C. It is noted that, for sake of simplicity, only one rubber container (4) is presented in a single storage/waste compartment (3). It is further noted that not necessarily all compartments are used, for example, the experiment may utilize only one or two of the three storage/waste compartments. The main compartment (2) (FIGS. 1A and 1D) was prepared from Polysulfone, and had a volume of 2 ml. Each storage/waste compartment (3) (see FIGS. 1A, 1B and 1D) contained rubber (Viton®) container (4) (shown separately in FIG. 1C), in which fluid may be stored. The volume of each storage/waste compartment (3) was 1 ml. The fluids in main compartment (2) may be mixed with the fluids from the rubber containers (4) attached thereto by activation of a designated plunger, which is used for the activation and in order to release the anti-solvent from the reservoir, as detailed herein.

In order to obtain optimal results in space, adjustment of the Vilanterol crystallization protocol to fit the system of the invention, and vice versa, was required. The original main compartment volume ranged between 0.1 to 1 ml. To maximize the amount of drug used in the experiment, and still meet the safety limitation approved by NASA, the main compartment (2) size was increased to 2 ml. The vilanterol concentration was adjusted according to the maximum temperature in which the payload could be stored on the ISS (37° C.). Tests showed that the highest concentration of vilanterol that could be dissolved in 37° C., using ethanol as the solvent, was 2.5% w/v.

Fluid from at least one storage/waste compartment (3), or more particularly, from rubber container (4), flowed into main compartment (2), to which storage/waste compartments (3), or more particularly, rubber containers (4), are attached, by activating the plungers (see FIG. 1D), which are located on top of storage/waste compartment (3), wherein the excess fluids were allowed to flow into the area of the plungers in the storage/waste compartment (3), which is used as dedicated waste compartments (see FIG. 2D). It is noted that according to other embodiments, the waste/overflow/excess fluids may be collected in dedicated waste compartments. It is noted that the waste fluids for each experiment were collected separately from the waste fluids of other experiments. Thus, there is no mixing of fluids between experiments in each main compartment (2) or in any of the storage/waste compartment. According to other embodiments, any appropriate mixing of waste or any other reagents, may be contemplated.

In addition, as detailed herein, it is noted that any of storage compartments (3) may be used as the dedicated waste compartments, i.e., during the experiment, fluid flows from storage compartment(s) (3), or more particularly, from rubber container(s) (4), into main compartment (2) and any waste and/or overflow flows back into storage compartment (3), which may be empty, or at least partially empty, after fluid therefrom flowed into main compartment (2) (in this respect, refer to FIG. 2D). In addition, it is noted, any of storage compartments (3) may be initially empty or essentially empty and therefore, during the experiment may be used as a waste compartment.

Any liquid from storage compartments (3) may be transferred into main compartment (2), in order to obtain the precipitation of crystalline vilanterol in the anti-solvent (heptane), wherein each of storage compartments (3) may comprise either a vilanterol solution or the anti-solvent, both of which are transferred to main compartment (2), which may also comprise either the vilanterol solution or the anti-solvent.

Examples 1a and 1b, as detailed below, were performed as follows: one rubber container (4), placed in one storage compartment (3), was filled with a vilanterol/ethanol solution, which was cooled for crystallization (see Example 1a). Further, for example 1b, main chamber (2) was filled with a vilanterol/ethanol solution, and a second rubber container (4), placed in a second storage compartment (3), was filled with the anti-solvent (heptane), wherein, as detailed below, heptane was allowed to flow from rubber container (4) into main compartment (2) in order to obtain vilanterol crystals. It is noted that any excess fluid/waste was allowed to flow back from main compartment (2) the area of plunger (6) in storage/waste compartment (3), i.e., above compressed rubber container (4), such that the second storage compartment (3) was used also as a waste compartment (see FIG. 1D). It is further noted that the third storage compartment (3) was filled with additional heptane, in case necessary; however, in this experiment, it was not used.

All of the details regarding the examples detailed here are non-limiting and therefore, any of the compartments may be filled with any appropriate materials that may or may not be mixed, as required.

Example 1a—Crystallization of Vilanterol from Ethanol Solution by Gradual Cooling Gradual cooling of the vilanterol ethanolic solution (25 mg/ml) in rubber container (4), placed in one storage compartment (3), was carried out by reducing the temperature from 37° C. to 4° C. by storing the container in a refrigerator inside the ISS until the return to Earth. The results obtained upon return to Earth show the vilanterol space grown crystals in rubber container (4).

Example 1b—Crystallization of Vilanterol in Space by Addition of Antisolvent

Vilanterol (250 mg) was dissolved in 10 ml ethanol to result in a vilanterol solution having a final concentration of 25 mg/ml. Main compartment (2) of cassette (1) (FIG. 1A) was filled with 2 ml of the prepared vilanterol/ethanol solution. In addition, one rubber container (4), placed in one storage compartment (3), was filled with 1 ml heptane (anti-solvent). Cassette (1) was kept at 37° C.

After 10 days from launch into space, one plunger was released thereby activating one rubber container (4) in one storage compartment (3), allowing 1 ml of heptane to flow into main compartment (2), which, as mentioned above, comprises the vilanterol/ethanol solution. This resulted in mixing at a 1-1 volume/volume ratio of the heptane and the vilanterol/ethanol solution. Thirty minutes later, cassette (1) was cooled down to 4° C. and stored in a refrigerator until return to Earth.

Figure 3:
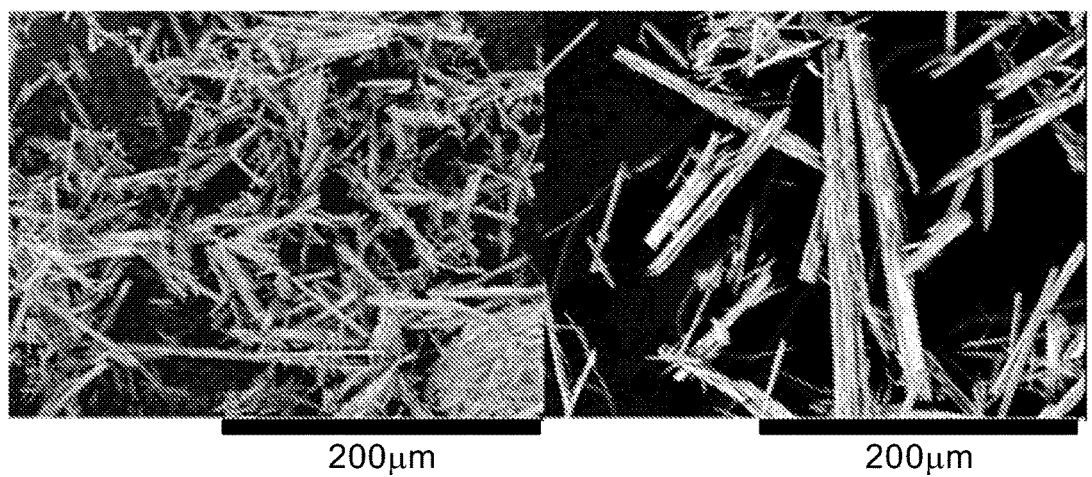
FIG. 3 shows two micrographs of crystals grown under 1 g gravity (left hand panel) and crystals grown in space, under microgravity (right hand panel), according to some embodiments of the present invention.
Figure 4:
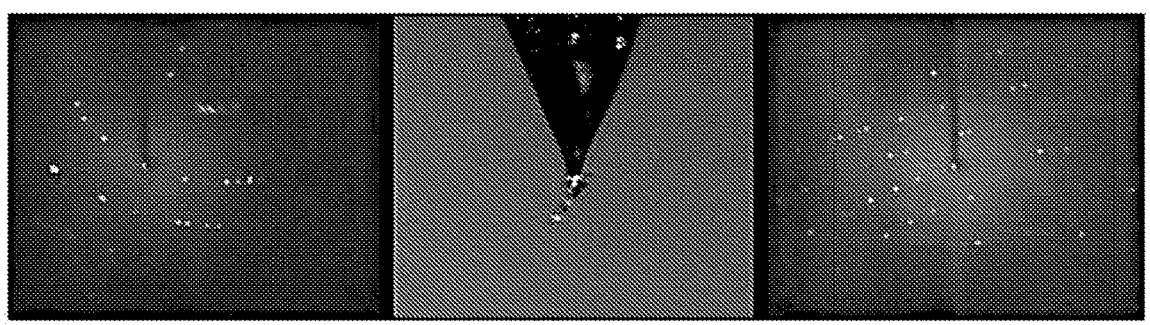
FIG. 4 illustrates the x-ray diffraction (XRD) of space grown (right panel) and earth grown (left panel) crystals, as well a single space grown crystal (center panel), according to some embodiments of the invention.

Results of Examples 1a and 1b—X-Ray Diffraction of Space-Grown Vilanterol Single Crystals The experiments performed in space on board of the ISS yielded crystals that were substantially larger and of higher crystalline order compared to their Earth-grown equivalents. See, for example, the micrograph in FIG. 3 taken by a scanning electron microscope, wherein the earth grown crystals are shown in the left hand panel while the space grown crystals are shown in the right hand panel. Particularly, in FIG. 3 it can be seen that the width of crystals crystalized on Earth are of only a few microns (FIG. 3, left hand panel) while the crystals crystalized in space under microgravity have a width of about 10-20 microns (FIG. 3, right hand panel). The width of the crystals, as well as the associated aspect ratio, i.e., the ratio between the length and the width of crystal, are of a critical importance for formulations prepared using the crystals. Generally, wider crystals in which the aspect ratio is relatively low provide a powder that has advantageous flow properties and, for example, will provide an advantageous inhalable formulation in which the flow properties of the powder are crucial. The quantity of material manufactured in orbit was sufficient for complete characterization study and further processing tests. The improved crystals were used to define the complete crystalline and chiral molecular structure of vilanterol by subjecting them to X-Ray diffraction crystallography study taken by a X-Ray diffractometer.

As presented in FIG. 4 the X-ray diffraction patterns show that the space grown vilanterol crystals (right-hand panel) are very well developed, having superior crystal morphology that has not been seen before. For example, the left-hand panel of FIG. 3, presenting the XRD pattern of earth grown crystals, presents a blurred, non-symmetric, X-Ray image, while the crystals prepared in space under microgravity, as shown in the right hand panel of FIG. 3, show a sharp symmetric pattern. The sharp symmetric pattern of the space grown crystals is a result of the high level of crystallinity obtained by growing the crystals in space. An example of a single space-grown crystal is shown, e.g., in the central panel of FIG. 4.

Example 2—Seeding on Earth of Vilanterol with Space-Grown Vilanterol Crystals (Prophetic)

A seeding experiment to produce vilanterol crystals on Earth using the space-grown vilanterol crystals will be carried out.

Seed material: vilanterol crystalized from ethanol by cooling from about 37° C. to about 4° C. aboard ISS in Nexus.

Seeding experiment: about 527 mg vilanterol will be dissolved in about 10 ml ethanol and heated to about 48° C. The sample will be cooled for over 12 hours to about 0° C. At about 43° C., the solution will be seeded with about 10.5 mg of dry crystalline space-grown Vilanterol. After cooling to 0° C. the sample will be stirred for about 1 hour and then filtered through sintered glass in a Buchner funnel.

The production of vilanterol by co-seeding with in-orbit manufactured vilanterol crystals may allow the formation of larger crystals as well as new drug polymorphs that may potentially improve the physicochemical properties of the vilanterol, thereby enhancing the drug performance as well as the bioavailability of the drug by offering, for example, better morphology for inhalation, controlled particle size and higher level of crystallinity.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for crystallizing molecules, said method performed in outer space and comprising:
   placing a molecular substance having a molecular weight equal to or lower than 500 Dalton in a microgravity environment, wherein the microgravity environment has a gravitational acceleration in a range of below 0.01 g to 0.000001 g;
   crystalizing molecules of the molecular substance in said microgravity environment, thereby obtaining at least one crystalline polymorph in said microgravity environment, wherein the molecules are crystallized by adding an anti-solvent to a solution of the molecules, by cooling a saturated solution of the molecules, by reacting the solution of the molecules with a solution containing ions, thereby forming an insoluble salt of the molecules, or by changing the pH of a solution comprising the molecules, thereby causing the molecules to precipitate in crystalline form; and
   removing the at least one crystalline polymorph from the microgravity environment by transferring it into an environment having a gravitational acceleration of 1 g; and
   wherein the molecules are active pharmaceutical ingredients (APIs).

2. The method of claim 1, wherein the molecules are selected from: vilanterol, a corticosteroid, a bronchodilator, a prostaglandin analogue and an anti-schizophrenic agent.

3. The method according to claim 1, wherein the API is vilanterol crystals.

4. The method of claim 3, wherein the vilanterol is crystallized by the gradual cooling of a saturated solution of vilanterol in a solvent.

5. The method of claim 1, wherein the solvent is a polar organic solvent or a combination of polar organic solvents.

6. The method of claim 1, wherein the polar organic solvent is an organic alcohol or a combination of organic alcohols.

7. The method of claim 6, wherein the organic alcohol is ethanol, methanol, iso-propyl alcohol, or any combination thereof.

8. The method of claim 1, wherein the solvent is a non-polar organic antisolvent or a combination of non-polar organic solvents.

9. The method claim 7, wherein the non-polar organic antisolvent is selected from, hexane, cyclohexane, heptane, pentane and any combination thereof.

10. The method of claim 4, wherein the method comprises (i) placing a saturated solution of vilanterol in the microgravity environment or preparing a saturated solution of vilanterol in a microgravity environment and (ii) subsequently to step (i), cooling the saturated solution in order to provide crystalline vilanterol.

11. The method of claim 3, wherein the vilanterol is crystallized by the addition of an antisolvent to a vilanterol solution comprising vilanterol and a solvent, wherein the anti-solvent is a non-polar organic solvent or any combination of non-polar organic solvents.

12. The method of claim 3, wherein the method comprises placing a solution of vilanterol in a microgravity environment or preparing a solution of vilanterol in a microgravity environment and subsequently, adding an anti-solvent to the vilanterol solution, thereby providing crystalline vilanterol.

13. The method of claim 1, further comprising preparing crystals in an environment having a gravitational acceleration of 1 g by seeding with the at least one crystalline polymorph prepared under microgravity.

14. The method according to claim 13, wherein the crystals prepared in an environment having a gravitational acceleration of 1 g have at least one crystalline property in common with the seeding crystals, prepared under microgravity, said crystalline property being selected from the group consisting of polymorph form, crystal habit, aspect ratio and particle size distribution.

* * * * *